United States Patent
Thomas et al.

(10) Patent No.: US 6,387,704 B1
(45) Date of Patent: May 14, 2002

(54) METHOD FOR COMPENSATING FOR THE TIME-DEPENDENT CHANGE IN COOLANT LEVEL DURING GAS SORPTION ANALYSIS

(75) Inventors: Martin A. Thomas, Lakeworth; Nicholas N Novella; Seymour Lowell, both of W. Palm Beach, all of FL (US)

(73) Assignee: Quantachrome Corporation, Boyton Beach, FL (US)

( * ) Notice: Subject to any disclaimer, the term of this patent is extended or adjusted under 35 U.S.C. 154(b) by 0 days.

(21) Appl. No.: 09/550,887

(22) Filed: Apr. 17, 2000

(51) Int. Cl.[7] .............................................. G01N 35/08
(52) U.S. Cl. ................. 436/55; 436/5; 436/8; 436/43; 436/50; 600/20; 702/30
(58) Field of Search ................. 436/55, 50, 5, 436/8; 606/20; 73/865.5, 38; 374/56; 417/205; 702/30

(56) References Cited

U.S. PATENT DOCUMENTS

| | | | |
|---|---|---|---|
| 3,589,167 A | * 6/1971 | Hill | 374/56 |
| 3,850,040 A | * 11/1974 | Orr, Jr. et al. | 73/865.5 |
| 4,305,291 A | * 12/1981 | Nelson | 73/865.5 |
| 4,566,326 A | * 1/1986 | Lowell | 73/865.5 |
| 5,058,442 A | * 10/1991 | Yamanaka et al. | 73/865.5 |
| 5,239,482 A | * 8/1993 | Ajot et al. | 702/30 |
| 5,360,743 A | * 11/1994 | Lowell | 436/5 |
| 5,408,864 A | * 4/1995 | Wenman | 73/38 |
| 5,637,810 A | * 6/1997 | Conner, Jr. | 73/38 |
| 5,674,218 A | * 10/1997 | Rubinsky et al. | 606/20 |
| 5,895,841 A | * 4/1999 | Lowell | 73/38 |
| 6,021,661 A | * 2/2000 | Lowell et al. | 73/38 |
| 6,257,835 B1 | * 7/2001 | Kachler | 417/205 |

* cited by examiner

Primary Examiner—Jill Warden
Assistant Examiner—Brian Sines
(74) Attorney, Agent, or Firm—Robert M. Schwartz; Gerald R. Hibnick

(57) ABSTRACT

For use in a sorption analysis system, a method compensating for measuring error due to the time-dependent evaporation of liquid coolant and the resulting change in the level of the coolant and temperature increase around the stem of the sample cell, during a gas sorption analysis of a sample in the sample cell. This error compensation does not inhibit coolant evaporation and is without recourse to mechanical means or other physical contrivances for causing the system to act as if the coolant were not evaporating. This method employs fixed and time-dependent data, including: changing coolant level and sample cell stem temperature changes, both of which can be obtained off-line, cold zone volume changes, and volumes of adsorptive gas transferred into the sample cell, to generate progressive error correction; whereby, system output is being corrected throughout the duration of the sorption analysis.

21 Claims, 7 Drawing Sheets

METHOD FOR COMPENSATING FOR THE TIME-DEPENDENT CHANGE IN COOLANT LEVEL DURING GAS SORPTION ANALYSIS

BACKGROUND OF THE INVENTION

1. Field of the Invention

This invention concerns sorption analysis and, more specifically, a method for compensating for the time-dependent change in the coolant level surrounding the sample cell during gas sorption analysis.

The measurement of the amount of gas adsorbed and desorbed by a solid as a function of gas pressure is employed in the determination of surface area, pore size, pore volume and pore area distribution of many solid substances. These substances can be non-porous or porous to a greater or lesser extent and can be in the form of monoliths, granules, pellets, tablets, extrudates, powders or other solid form. The surface area of a solid is an important physical characteristic which plays a significant role in the behavior of the solid in terms of its interaction with other solid surfaces, liquids, vapors and gases. Pore size, volume and area distributions are important in catalyst selectivity, molecular sieving action, gas and liquid absorption capacity, optical properties of transparent materials and bio-compatibility of implanted materials.

The method most commonly employed to make these surface area and other determinations is the so-called static volumetric method and requires that the amount of gas adsorbed be measured as a function of applied gas pressure. In this method, the sample is contained in a sample cell normally constructed of borosilicate glass. Suitable pretreatment of the sample removes unwanted surface contaminants. The sample cell containing the sample then is attached to the measuring apparatus and evacuated to remove much of the residual atmosphere or other gas. A valve separates the test station, to which the sample cell is attached, from the remainder of the system. The void volume is that volume contained within the sample cell and the test station up to that valve and must be known in order to calculate the amount of gas in that void volume. This void volume determination can be achieved in one of at least two ways. In the classical technique, the void volume is measured immediately prior to the sorption analysis. A non-adsorbing gas, such as helium, is expanded or dosed from a known, calibrated volume, the dosing manifold, into the sample cell containing the sample. The principles of the gas laws, primarily Boyle's Law, are applied. This determination must be done both at ambient temperature and then with that portion of the cell containing the sample at the analysis temperature. Alternatively, and in the preferred embodiment of the invention, the void volume is not calculated directly, but the amount of analysis gas, the adsorptive that is transferred from the manifold to an empty cell, is measured as a function of pressure, under the same conditions of temperature as the subsequent analysis, and can be done at one or more discrete pressures.

The analysis temperature normally is no higher than the boiling point of the adsorptive gas. Since the analysis gases most commonly employed are inert, "permanent" gases, the analysis temperature should be that of the liquefied gas. This enhances the adsorption process; therefore, a cryogenic liquid is employed. For example, when nitrogen is used as the adsorptive, the cryogenic liquid most commonly is liquid nitrogen and is held in a Dewar flask into which the sample cell is immersed. After the void volume has been determined in the manner described above, the proportion which is effectively at ambient temperature, the so-called "warm zone", and that which is effectively at the cryogenic temperature, the so-called "cold-zone", must remain constant. Only then can the amount of gas in the total void volume be accurately accounted for.

During an adsorption analysis, for an accurate determination to be made, pressure in the sample cell must increase solely due to the addition of gas from the dosing manifold and not due to the warming of any portion of the void volume. However, during the measurement, the coolant evaporates from the Dewar. Thus, the cold zone decreases in volume, while the warm zone increases. If this change of coolant level is not compensated for by some means, the measurement of the amount of gas adsorbed is in error, which is a function of both pressure and time.

At low pressures, there exists less gas in the void volume than at higher pressures. Therefore, any change in temperature at low pressure imparts a smaller error than an identical change at a higher pressure. Since the affected volume increases with time, it is essential to make the compensation also a function of time. During a complete adsorption/desorption isotherm analysis, the pressure in the cell increases during adsorption, then decreases during desorption, due to the normal measurement process. In this case, there exist two data points for each pressure value, one adsorption and one desorption. However, even though the pressure in the cell might be identical, the data points never can be recorded at the same instant in time and therefore the degree of compensation or i.e. the amount by which the sorption data is to be corrected, is not identical.

2. State of the Prior Art

Control or maintenance of cryogenic liquid level, the coolant, which surrounds the sample cell, which is changing because of its continuing evaporation, can be achieved in a number of ways:

a) The coolant can be replenished during the analysis by transferring coolant from a storage vessel to the Dewar, in response to the output of an electronic circuit monitoring coolant level, as employed in Micromeritics® Digisorb 2600, Coulter® Omnisorp® 100/360 and Carlo Erba Sorptomatic.

b) The analysis Dewar can be raised by a motorized elevator in response to the output of an electronic circuit monitoring the coolant level, as in the Quantachrome Autosorb.

c) A porous tube, placed around the stem of the sample cell, draws coolant up to the top of that tube by capillary or wicking action, regardless of coolant level around the porous tube, as in several products of Micromeritics.

The changes in the amounts of gas in the cold and warm zones of the void volume, due to the uncontrolled evaporation of coolant, can be minimized in a number of ways, for example d), e) and f), next described; which can be used alone or with any of a) through c):

d) The stem portion of the sample cell is made as narrow as reasonably practical. This reduces the actual volume affected by coolant level change.

e) The void volume can be reduced further by the use of filler-rods, as taught by U.S. Pat. No. 5,360,743, Lowell. Extreme amounts of said volume filling can be achieved by the use of rods manufactured from polytetra-fluoroethylene (PTFE), as in the Quantachrome® NOVA® analyzer, and can be machined to provide a tighter fit than can rods made of glass.

f) The stem portion of the cell can be insulated from the coolant by means of a tight-fitting jacket of material with poor thermal conductivity, or by containment within an evacuated or partially evacuated vessel, which can be silvered as in the manner of a Dewar flask.

The problems with the prior art control means are that a) through c) require some physical contrivance to actually control the coolant level, which can be less than successful and entails added costs, risk of mechanical and/or electrical failure and normally sets limitations as to the type and size of sample cell and/or Dewar. The narrow stems of d) and e) set limitations as to the size of sample which can be admitted into the sample cell. Also, tight fitting filler rods can limit evacuation rates of the sample cell; evacuation being a prerequisite for this type of volumetric analysis. Insulation means f) is not particularly effective, since it is exactly this type of construction in the surrounding Dewar which is unable to maintain the coolant level, in the first place. Furthermore, this prior art adds significant extra cost to the fabrication of the sample cell and increases fragility.

SUMMARY OF THE INVENTION

This invention provides method usable with sorption analyzers for temperature compensation due to coolant level changes around the sample cell. Coolant level changes are due to progressive evaporation of the coolant in the Dewar and cause relative temperature changes in cold and warm zones of the void volume of the analyzer. Such temperature changes generate time-dependent errors in the sorption analysis. This invention, throughout the duration of a gas sorption analysis, in "real time", provides temperature compensation, without the need for any physical or mechanical contrivances. Thus, this invention enables correction of the error, otherwise introduced due to the changes in cold and warm zones, in the determination of volumes of gas adsorbed and desorbed. This invention permits the coolant to evaporate and, in "real time", provides for mathematic corrections to the sorption data and the output from the analyzer; a novel solution to the problem.

The determination of the change in the volume of the cold zone and the amount of gas in the ever increasing warm zone requires the use of known as well as easily ascertained data, determination of other and variable information and the use thereof in formulas, which themselves are known to those skilled in the art, but are employed in a novel manner. One piece of predetermined information is ($\Delta H$), the changing level of the evaporating coolant, which can be predetermined experimentally by the manufacturer or by the analyzer user and stored, as in a lookup table, in the analyzer program; can be plotted graphically and then curve fitted by equation. See equation (A) further below. The changing coolant level ($\Delta H$) also is employed in a known formula (B) set forth below to obtain the value for the decrease in adsorptive gas in the cold zone ($\Delta V$ cold zone) over a given time period. The change of that affected portion of the cold zone temperature also is a needed piece(s) of data.

DETAILED DESCRIPTION OF THE INVENTION

Figure 1:
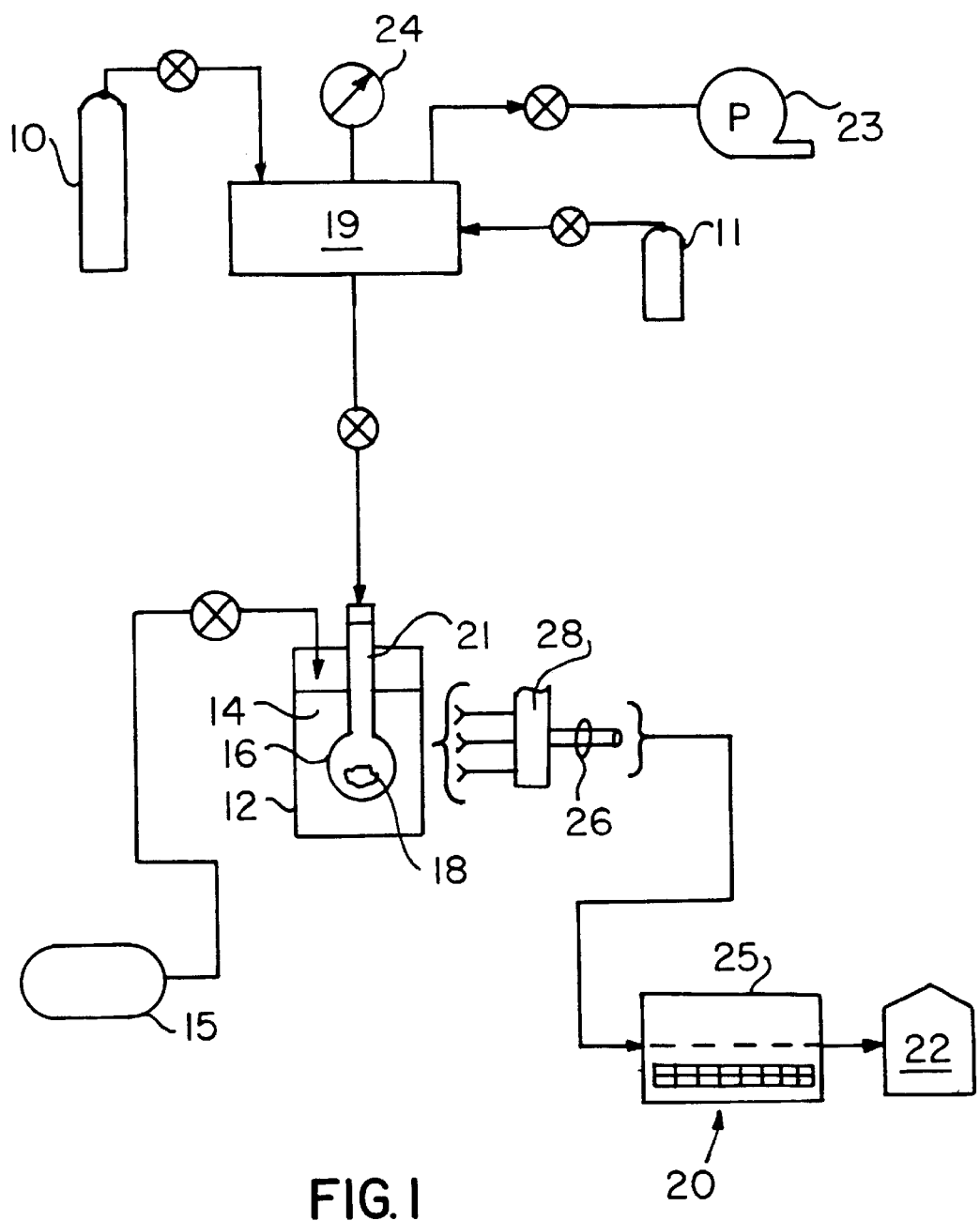
FIG. 1 is a diagram of the typical sorption analysis system equipment.

Those skilled in the art of gas sorption analysis fully appreciate that the basic system equipment, as shown in FIG. 1, includes: a source 10 of gas, such as nitrogen, under pressure; a source 11 of gas, such as helium, under pressure; a container 12, termed a Dewar, for coolant 14, such as liquid nitrogen, fed or prefilled from source 15; a sample cell 16 to contain a sample 18 to be analyzed; a valved manifold 19 coupled between the sources 10 and 11 and an input to the sample cell; and various conduits, valves, pressure measuring means, sensors, etc. linking the equipment. Also, basic to the analysis equipment is a computer 20, having the capability of receiving and storing fixed and variable input data; and a readout means 22, both digital and graphic. In most laboratories which accomplish gas sorption analysis, the analyzer uses only one Dewar 12, but might have an extra or back up Dewar, and would have a few sample cells 16, usually of the same and different volumes for extras and for different sample types and volumes. For convenience of operation of the system, the identification of each Dewar 12 and sample cell 16 would be stored in the computer 20. Such identification can include known parameters/data, such as: the volume and internal diameter of the specific Dewar, initial weight of the Dewar when filled with coolant to a specific level, the density of the liquid coolant, external and internal diameter of the stem 21 of the sample cell, the external diameter of any filler rods (not shown in FIG. 1) for the stem, the volume of the manifold 19, etc. Also, the system would have vacuum pump means 23 for evacuating the manifold 19 and the sample cell 16.

Figure 2:
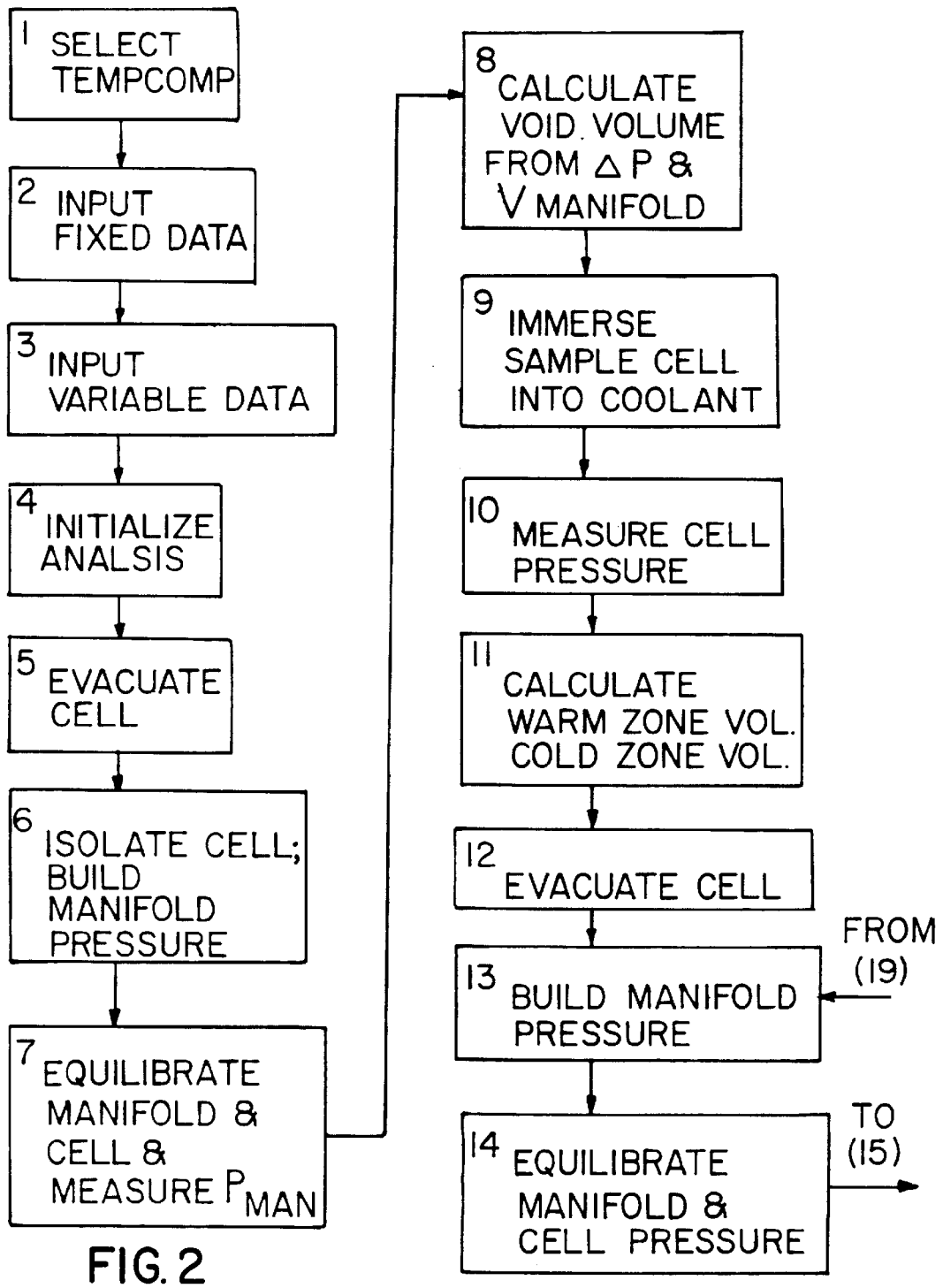
FIG. 2 is a flow chart of the operative steps used in the invention.
Figure 2:
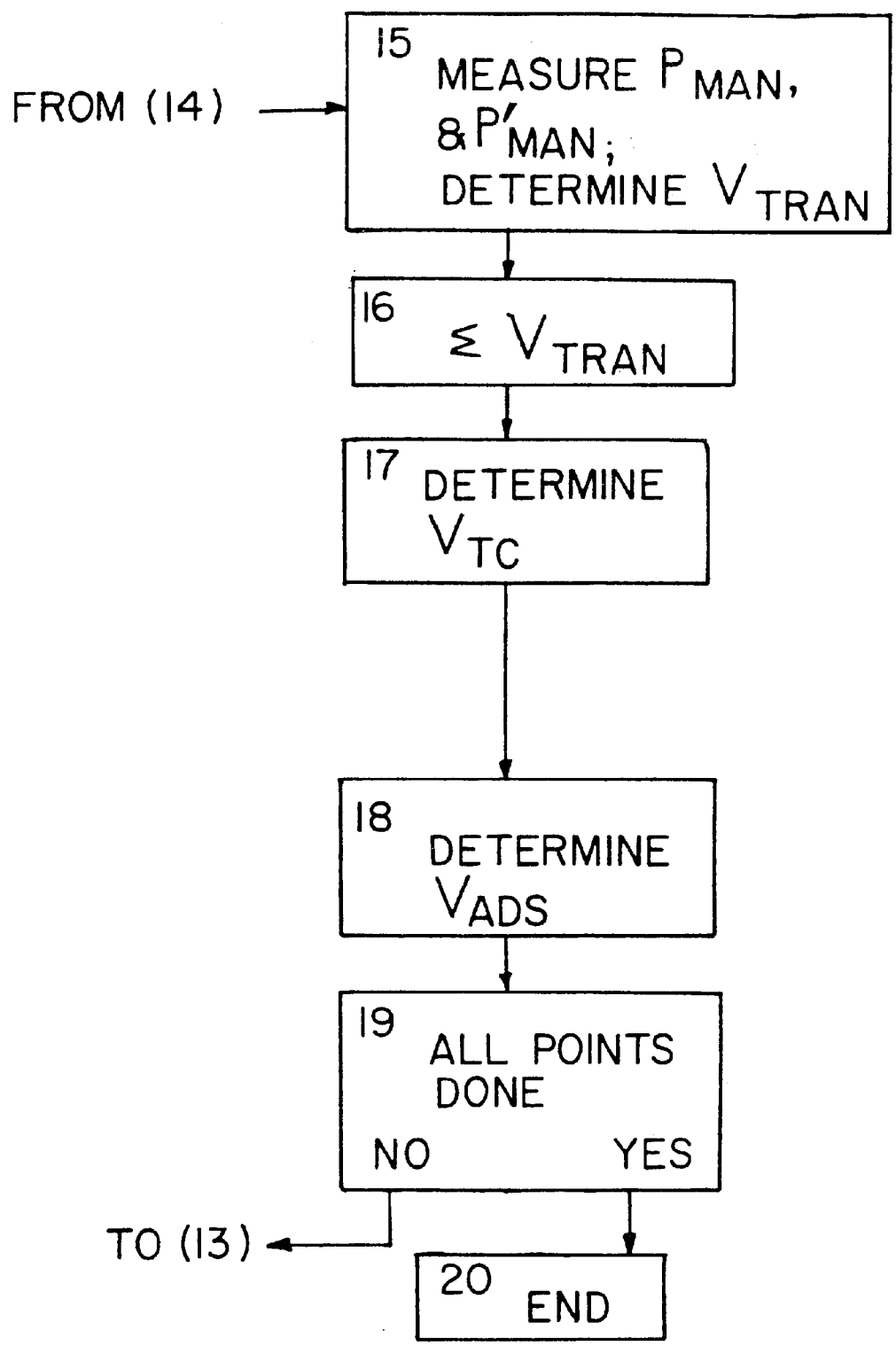

The sorption system also contains meter means 24 for measuring manifold and sample cell gas pressure at any required time. Based upon stored data and dynamically changing data, the computer 20 can accomplish mathematic tasks, including employing specific polynomials and their coefficients, which can be employed with the present invention. The readout means 22 provides the digitized text and plotted information, curves, etc. pertaining to the sorption analysis, as it is being developed over time. A complete analysis, adsorption and desorption can take more than one day, as shown in the plots in FIGS. 3 and 4. The computer 20 also contains a program controller portion 25, which executes one or more established programs, step-by-step. One of the established programs would be the temperature compensation program "TempComp"™ of this invention, one generic embodiment being shown in the flow chart of FIG. 2.

The following description of the program steps is not intended to cover all steps, subroutines, etc. of the actual program/process of the system, but only the major steps to implement one useful embodiment of the "TempComp" invention program. Different computer systems, using different programming approaches, can be employed to reach the same temperature compensation goal. Also, different sorption analyzers, from the same as well as different manufacturers, could require different programming. This invention is capable of being retrofit into existing sorption analyzers.

Not set forth herein are all of the routine tasks for preparing a sample 18, placing it into the sample cell 16, loading the coolant 14, such as liquid nitrogen, from the source 15, into the Dewar 12, zeroing the system, presetting the system, entering fixed information/data, etc. etc. In a more sophisticated system the fixed data would be stored for easy retrieval. Variables would be called up by "prompts", with choices of variables previously stored in the computer memory. Hence, and with reference to the flow chart in FIG. 2, the first working step could be "#1/select TempComp Sample Analysis"; to call up this unique invention and enable the system to function in a TempComp mode. If the computer 20 with its program controller 25 had already in storage all of the needed fixed data information, the sample 18 was in the sample cell 16, the changing coolant level ($\Delta H$) predetermined or to be determined, and the weight of the filled Dewar were stored, the program could advance through the next several steps.

The ($\Delta H$) coolant level for a specific Dewar can be stored in the system program/data base by the manufacturer or the user; or it can be determined by equation A as follows, in which W is the weight (mass) of the coolant, the coolant level in the Dewar is (H), (V) is the volume of the Dewar, ($\rho$) is the density of the liquid coolant, (D) is the internal diameter of a circular cross-section Dewar and ($t_i - t_{i-1}$) is the elapsed time;

$$\Delta W = W_i - W_{i-1}; \Delta V = \Delta W / \rho; \text{ thereupon}$$

$$\Delta H = (\Delta V \cdot 4 / \pi) \cdot D^2 \quad\quad\quad A:$$

The change of weight $\Delta W$ is measured "off line" by an accurate scale, over numerous time periods, which can correspond to the BET points, as well as subsequent points in the duration of the sorption analysis.

Figure 3:
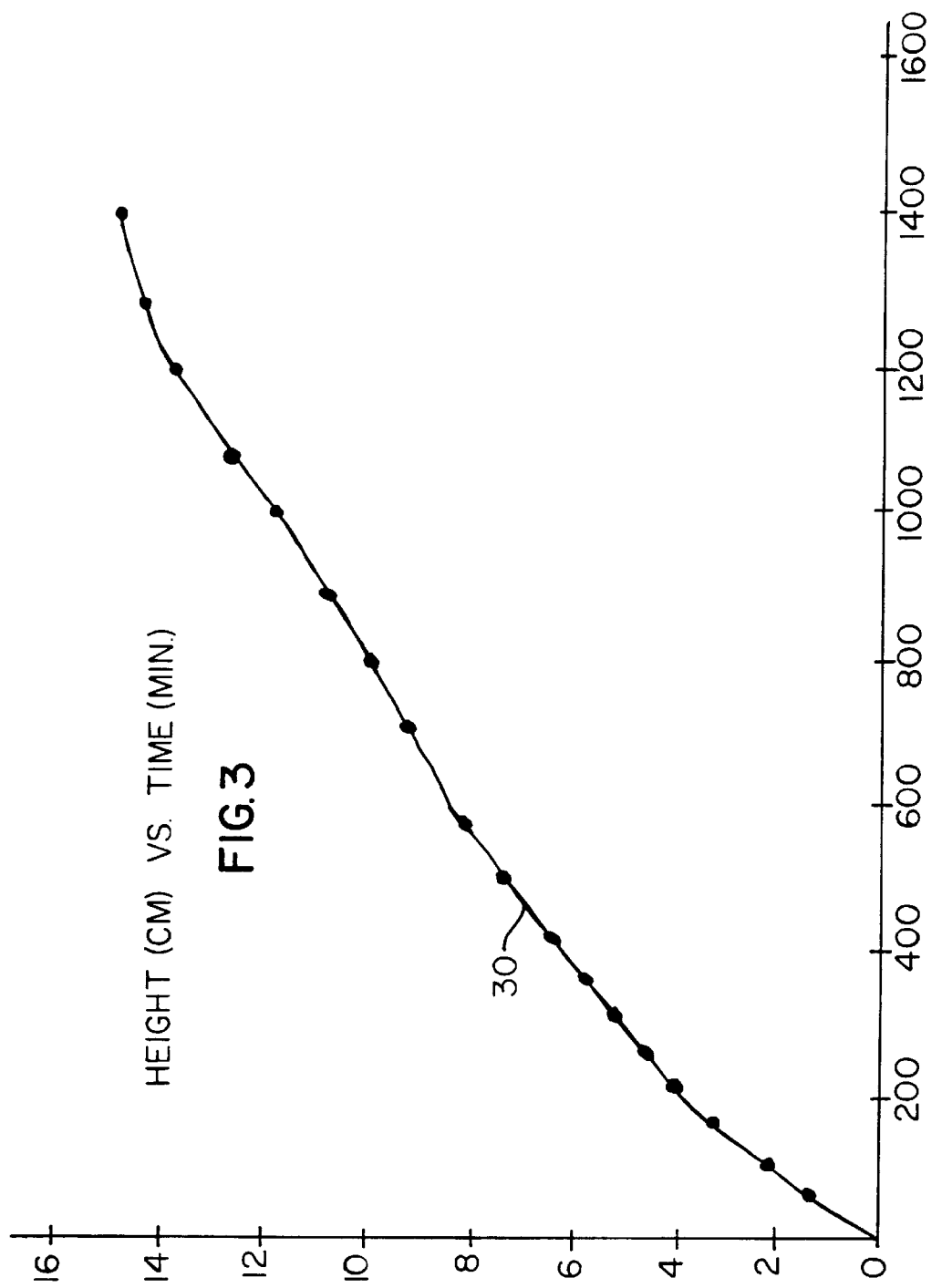
FIG. 3 is a plot of coolant height vs. time, based upon experimental data.
Figure 4:
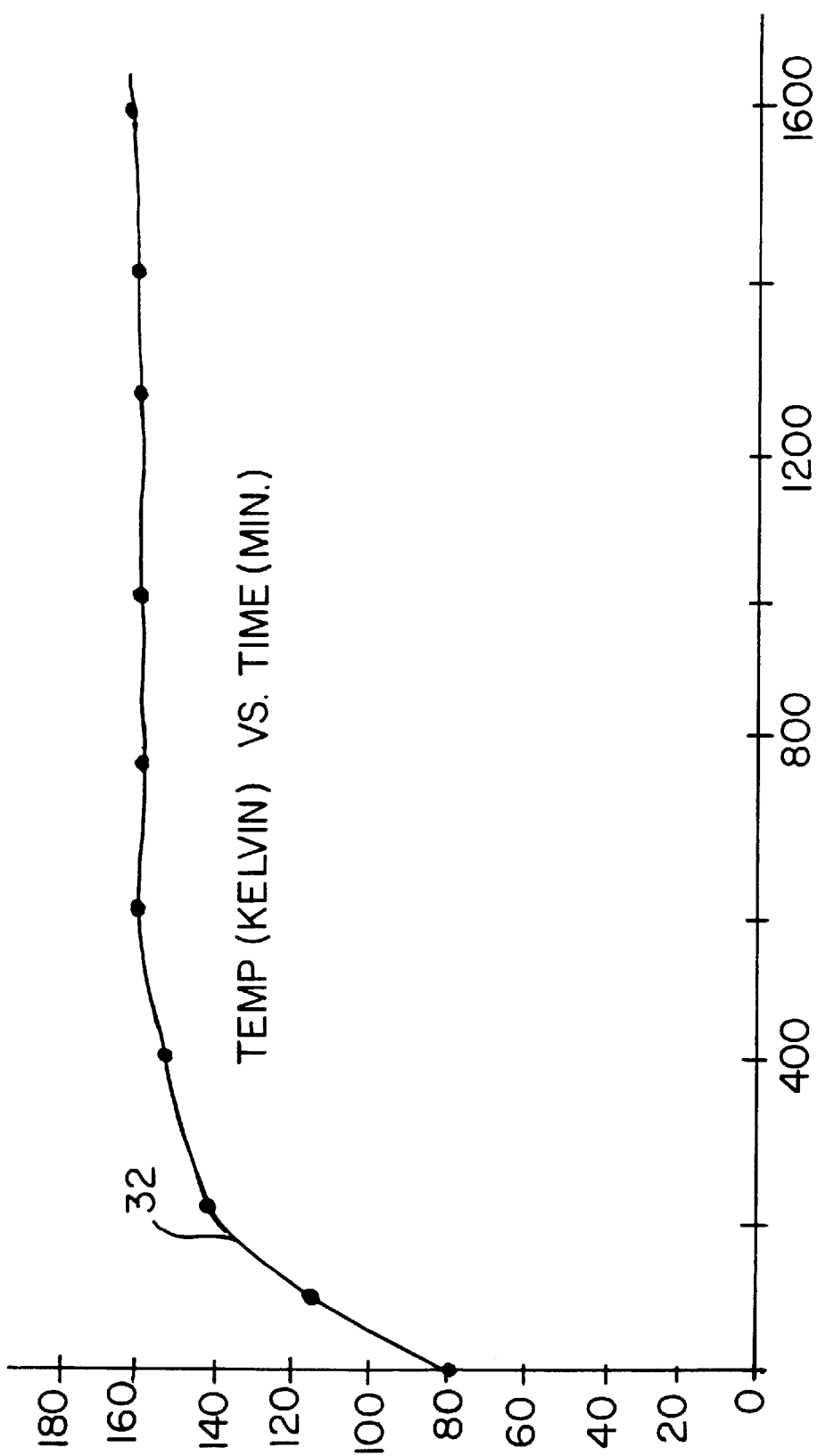
FIG. 4 is a plot of effected cold zone temperature vs. time, based upon experimental data.

Once this changing coolant level ($\Delta H$) is determined, it can be loaded in the computer 20, and recalled/used during analysis, at each specific datum point. However, the storage of such a look up table might not be practical, due to computer memory capacity, etc. Hence, once the ($\Delta H$) data is obtained off-line, it can be used with a conventional curve fitting formula to create a specific equation, which is stored and used via the computer 20 and its program controller 25. One such curve fitting formula (also called a trendline calculating equation) is a least squares fit polynomial:

$$y = b + c_1 x - c_2 x^2 + c_3 x^3 \ldots - c_6 x^6,$$

where b and $c_1 \ldots c_6$ are constants. Applied to the specific use in the "TempComp" process, y=($\Delta H$) in centimeters; x=time in minutes; and the constants b and c are those which will yield a curve 30, which is shown in FIG. 3, which accurately replicates the experimentally obtained curve ($\Delta H$), shown as 30 in FIG. 3.

One of various commercially available software programs to achieve the desired curve fit is Microsoft® Excel 97 SR-1. By initially choosing a relatively few points along the x-axis (time) and permitting the software to number crunch and develop an x-y plot, the user of the software can achieve progressively closer approximations to the desired curve 30, that which was experimentally obtained, by shifting the time points. For fitting the coolant changing level curve ($\Delta H$) for a commercial Quantachrome sorption analyzer, for which the experimental curve 30 was plotted over fourteen hundred minutes and the level of the coolant evaporated over fifteen centimeters only nineteen time points were needed for the curve fit. The resulting polynomial (rounded off) was:

$$\Delta H = (0.1119) + (0.0247)t - (0.3324 \times 10^{-6})t^2 + (0.2933 \times 10^{-10})t^3 - (0.9133 \times 10^{-15})t^4.$$

However, for purposes of this example, let it be assumed that not all fixed and known variable data were previously entered into the system computer memory. Accordingly, the program controller would advance to step #2 and determine if all known or fixed data had been input/stored. If not all present, there would be displayed on the screen of the computer 20 and/or readout 22 a request for the missing data, such as the identification of the specific Dewar 12 and the specific sample cell 16. After manual input of the needed data, the program controller 25 would advance to step #3 and determine if all variable data had been supplied and stored. If not, there would be displayed and/or printed out one or more prompts, such as "sample weight?" Examples of fixed data and variable data typically needed in program steps #2 and #3 are: sample cell I.D., which includes the internal diameter of the sample cell (Dcell), and the external diameter of the stem filler rods (Drod) if the rods are used; the Dewar I.D., which includes the internal diameter of the Dewar flask (D) and its volume (V); the density ($\rho$) of the liquid coolant; the ($\Delta H$) of the coolant; the weight (W) of the filled Dewar; the initial temperature and rate of temperature change of the cold zone; the number of BET points;

The computer 20 also would have in memory/storage formulas needed to be used with the fixed and variable data such as the formulas A, B, C, D and the curve fitting polynomials set forth herein, to accomplish the error correction—the "TempComp". Certain of the initial information and the progressively changing data would be transmitted via data lines 26 into the computer, from a sensor array 28 coupled to selected portions of the Dewar, sample cell, gas pressure meter, void volume zones, etc., as is well known in sorption analyzers.

Once the sorption analyzer is satisfied that preconditions have been met, the program controller 25 will advance to step #4 and advise the human operator that Analysis can be initialized. Thereupon, the system goes through a series of routine sorption analyzer steps: #5 evacuate the sample cell 16 by the pump 23, via the manifold 19; #6 isolate the sample cell by the valve between it and the manifold and build up gas pressure in the manifold 19 from the gas source 11; #7 open the valve between the manifold and the sample cell, and wait until pressure equilibrium, measure the new pressure (P) in the manifold and transmit that pressure (P) to computer storage; #8 calculate the void volume (Vcell) of the sample cell from knowing the volume of the gas, such as Helium, which was transferred from the manifold, having a known volume (Vman), into the sample cell, and the change of pressure ($\Delta P$) in the manifold; and store that void volume value. The next step #9 causes the sample cell to be immersed in the Dewar which contains the coolant. This is accomplished by raising the Dewar to a predetermine position, which then remains fixed for the remainder of the sorption analysis.

It is to be clearly understood that, for the remainder of the sorption analysis, which can take many hours, there is to be no relative vertical motion between the Dewar and sample cell; nor is there any replacement of the evaporating coolant in the Dewar. Nor are there any "contrivances" (wicks, etc.) to cause the system to believe that the coolant is not evaporating.

Next, in step #10, the pressure change in the cooled sample cell is measured and stored. Thereupon, in step #11, the warm zone and cold zone volumes are determined. The cold zone volume is determined from existing data. Then, it is subtracted from the previously known and stored value of the void volume, to obtain the warm zone volume. The changing cold zone volume ($\Delta V$ gas cold) is obtained from equation B.

$$\Delta V \text{ gas cold} = (\Delta H \pi / 4) \cdot (Dcell^2 - Drod^2) \cdot (P/760); \quad\quad B:$$

in which the change in coolant height ($\Delta H$) and the absolute manifold pressure (P) are at a specific point in time, as compared to a previous point in time, as well at a starting point in time (t=0). The value 760 is the standard condition (STP) at which time (ΔH) and (P)=0 in mmHg. during a given time period (i-1). In steps #12, 13 and 14, the sample cell is evacuated, the manifold pressure is built up from the adsorptive gas source 10, to a required amount (Pman), and the valve between the manifold and the sample cell is reopened to enable pressure equilibrium therebetween. In step #15, the new pressure of the manifold (P'man), which then is the pressure in the sample cell, is measured; and it is used to calculate the total volume of the adsorptive gas transferred into the sample cell by the equation C:

$$V_{TRANS}=(Pman-P'man)/760 \cdot Vman \qquad C:$$

The volume of the gas thus transferred is recorded and, if this was other than at the first data point of the sorption curve, is added, in step #16, mathematically to the amount(s) previously transferred in step #15 for the previous data point(s), to obtain the current or total ($\Sigma V_{TRAN}$) transferred value.

In as much as the coolant level is receding from around the stem 21 of the sample cell 16, the thus exposed portion of the stem becomes warmer as a function of time. Such changing temperature (T) is required data and can be estimated, measured in real-time by a sensor, obtained to yield a look-up table, or mathematically determined. In a preferred embodiment of the "TempComp" process, (T) is determined in a way very similar to (ΔH). First, off-line, without need of any sample 18; hence not in "real-time", the change in stem temperature of the affected is measured as the liquid coolant 14 evaporates from around the upper portion of the stem 21, progressively during the length of time typical of a full sorption analysis; and that changing temperature data is used to define an experimental temperature in kelvin v. time in minutes the graph 32, shown in the plot of FIG. 4. Then, a curve fit formula, such as the polynomial employed in the Microsoft® Excel 97 SR-1, is used with a few data points (x=time t; y=Temperature T) to create a curve fit equation that closely matches the experimentally obtained curve. When used with a Quantachrome sorption analyzer, to create the experimental curve, over a period of sixteen hundred minutes and a temperature change from 77.4° K. to about 165° K., the polynomial needed only seven points to closely approximate the experimental curve 32. The resulting equation was (rounded off):

$$T=77.3999+(47336 \times 10^{-5})t-(10819 \times 10^{-7})t^2+(12679 \times 10^{-1})t^3-(79544 \times 10^{-14})t^4+(25429 \times 10^{-17})t^5-(33 \times 10^{-18})t^5,$$

and can be stored in the computer 20 for recall at each datum point.

Next, in process step #17, there is determined the temperature corrected volume (VTC) of the volume of transferred adsorptive ($\Sigma VTRAN$) obtained in step #16. Equation D is employed in step #17 as follows:

$$V_{TC}=\pi(r\ cell^2 - r\ rod^2) \cdot (\Delta H)+(T/77.4) \cdot (P/760); \qquad D:$$

in which (77.4) is the temperature in kelvin of the liquid coolant, (P) is the absolute gas pressure in the sample cell in mmHg at that time, and 760 is the standard condition pressure STP.

At this juncture, all needed information has been obtained for attaining the goal of the corrected value of the total volume of the adsorbate (VADS) used up to any specific datum point in time, for example, a BET point. Process step #18 employs Equation E and provides this answer as (VADS).

$$V_{ADS}=(\Sigma V_{TRANS})-(V_{TC}+V_{WARM\ ZONE}+V_{COLD\ ZONE}). \qquad E:$$

Figure 5:
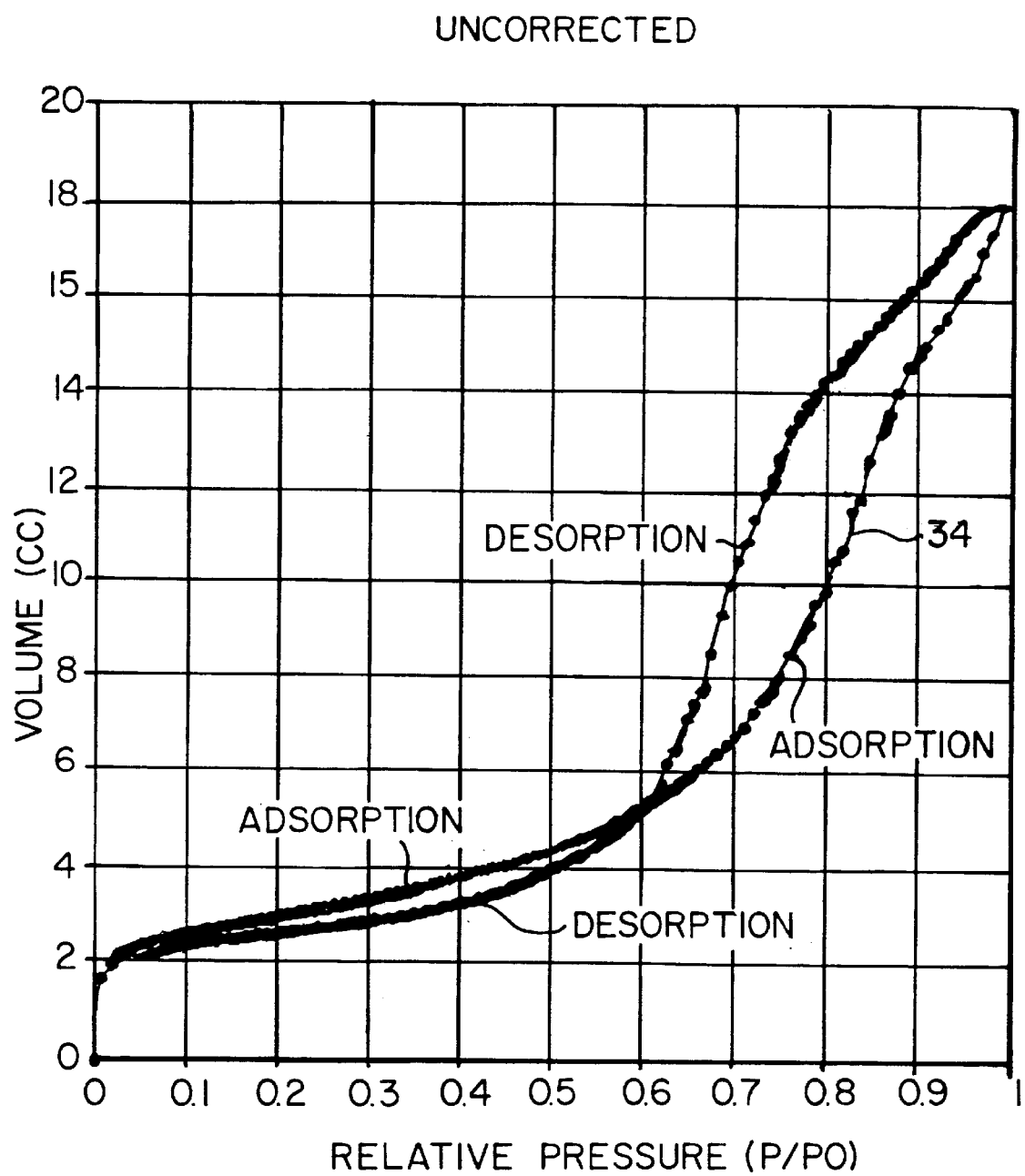
FIGS. 5 and 5a show uncorrected and corrected sorption curves, and the amount of correction obtained by this invention.

This corrected volume of adsorbate is stored, and recorded by the computer 20 and the readout device 22, for one of the x-y values of the sorption isotherm shown in solid line 34 in FIG. 5; "x" being the time and "y" being the corrected adsorbate volume.

Assuming that additional data points are to be determined, the program controller 25 advances through the next step #19 and back to step #13. Whereupon, steps #13 through #19 are repeated as a loop, with need and use of data for the next isotherm points, to yield x-y output for the next value on the isotherm 34. This process loop of steps #13 to #19 is repeated until all BET and isotherm points are obtained and the sorption analysis is completed. During each cycle through this process loop, many of the data values are different, especially including the coolant height and temperature (ΔH) and (T)corrections.

Figure 5A:
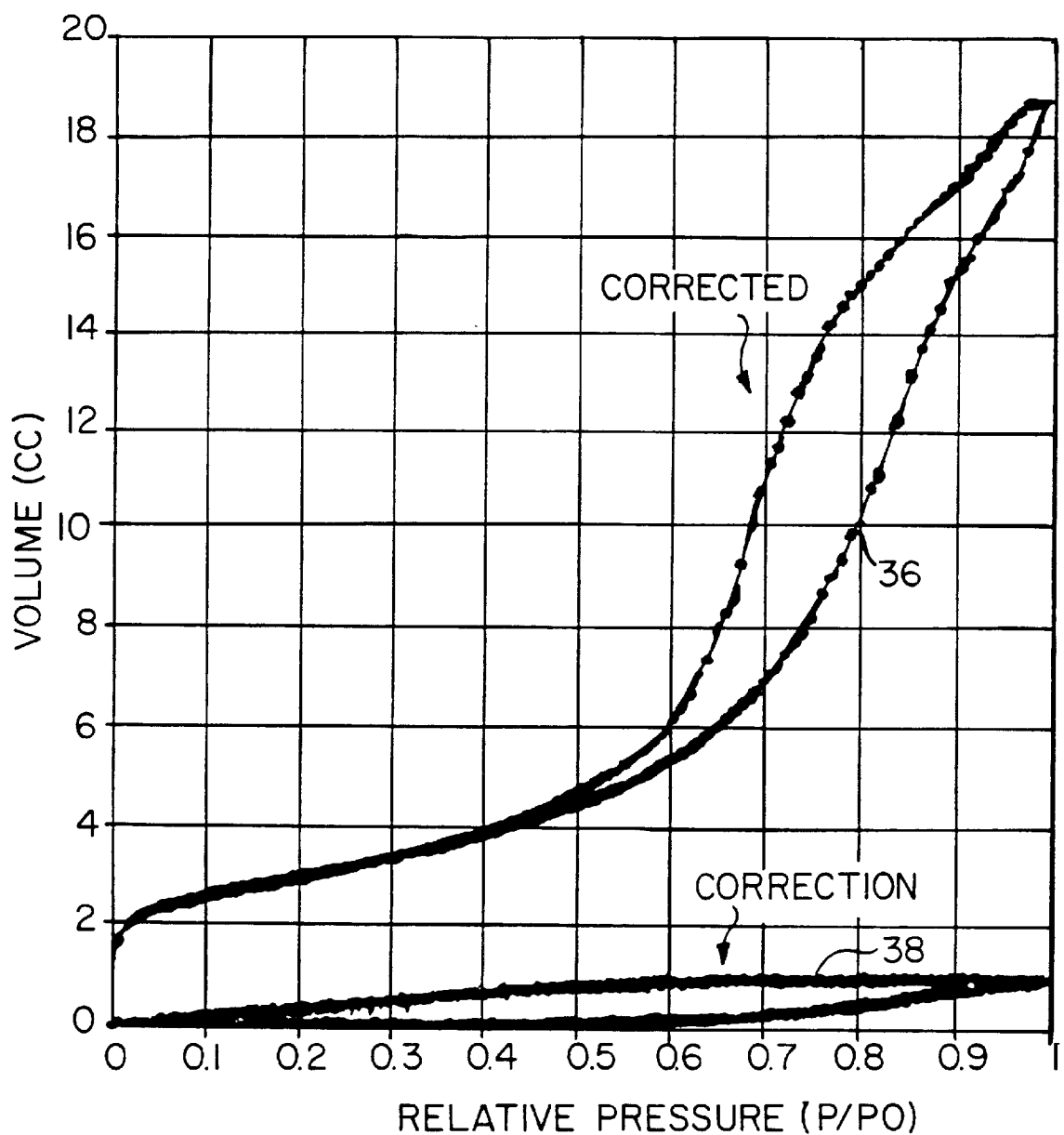

From viewing the uncorrected isotherm 34 in FIG. 5 and its corrected isotherm 36 in FIG. 5a, one can appreciate the significance of the (VTC) correction, shown in FIG. 5a as curve 38, obtained point by point, from step #17 and applied to the isotherm 34 to attain the "TempComp" corrected isotherm 36.

As is well known to those who operate sorption analyzers, often there is not required a complete sorption and desorption analysis. In fact, there are circumstances where only a few BET points are needed, covering one hour or less. Such short-time analysis, as well as longer, but not full sorption analysis, is fully within the capability of the present compensation process invention. The operator merely needs to select the points of interest and the compensation for that span of time will result.

It is recognized that many present and future sorption analyzers will operate with different process methodologies, quite apart from compensation for coolant evaporation and temperature warming around the stem of the sample cell. Many sorption analyzers have and will have unique calibration techniques and other subroutines which, when combined with/integrated to employ the compensation criteria of the present invention, will result in a step-by-step process which does not follow the generic process steps shown in FIG. 2 and detailed in this Specification. Nevertheless, the herein taught approach to compensation for both coolant level lowering by evaporation and the resulting temperature increase around the stem of the sample cell, preferably employing off-line gathered data; and without coolant level mechanical change, etc. can result in state of the art sorption analysis, which lies within the spirit and scope of the claims appended hereto.

What is claimed is:

1. In a method for conducting sorption analysis in a sorption analyzer system, a test sample being in a sample cell and the sample cell being in a Dewar, there being liquid coolant in the Dewar at a certain initial height level and surrounding the sample cell; the sorption analysis progressing over a length of time, during which the liquid coolant evaporates from the Dewar, the improvement comprising the steps of:
   a) establishing a relative vertical relationship between the sample cell and the Dewar;
   b) fixing that vertical relationship for the duration of the analysis;
   c) permitting the liquid coolant to evaporate over time, thereby lowering its level within the Dewar and around the sample cell;
   d) letting said lowering of coolant level result in time-dependent temperature changing of a stem portion of the sample cell;

e) allowing, by said temperature changing, time-dependent errors to occur during the sorption analysis;

f) correcting for such time-dependent errors by:
  i) utilizing fixed and time variable sorption analyzer system data, such data being exclusive of direct measurement of time-dependent coolant level lowering in the Dewar during the sorption analysis of the sample;
  ii) obtaining time-dependent compensating data from said step of utilizing; and g) compensating for the time-dependent temperature changing over the length of time of coolant evaporation with use of the compensating data.

2. The method according to claim 1 in which, the duration of the sorption analysis is divided into numerous time periods, and sorption analysis data is gathered at each time period for generating discrete data outputs for each period, said method further comprising the steps of:
  a) pre-determining the weight of the coolant for each time period and thereby;
  b) ascertaining the rate of coolant evaporation, for use during sorption analysis of a sample.

3. The method according to claim 2 including the steps of:
  a) supplying, during said time periods, differing volumes of adsorptive gas to the sample cell;
  b) verifying the volume of adsorptive gas supplied during each specific time period;
  c) totaling that volume with the volumes of adsorptive gas supplied over previous time periods; and
  d) applying, from said step of obtaining time-dependent compensating data, compensated values for the volumes of adsorptive gas.

4. The method according to claim 3 in which, a gas manifold supplies adsorptive gas under pressure to the sample cell, and said step of verifying includes:
  a) charging the manifold to a specific pressure prior to said step of supplying;
  b) equilibrating the gas pressure between the sample cell and the manifold; and
  c) detecting the change of gas pressure in the manifold upon said equilibrating.

5. The method according to claim 2, further including the step of:
  using the rate of coolant evaporation as time-dependent data during the sample sorption analysis.

6. The method according to claim 5 including the step of:
  storing, in a look-up table, data based upon the time-dependent rate of coolant evaporation.

7. The method according to claim 1, further including the steps of:
  a) creating experimental evaporation data regarding the time-dependent coolant evaporation;
  b) forming a time-dependent experimental curve from that experimental evaporation data;
  c) matching a curve fitting formula to that time-dependent experimental curve; and
  d) employing that curve fitting formula in said step of correcting for such time-dependent errors.

8. The method according to claim 7 in which, said step of matching includes:
  a) selecting specific time points from the experimental evaporation curve; and
  b) inserting those time points into the curve fitting formula to enhance said matching.

9. The method according to claim 8 in which, the sorption analysis ascertains data at certain times, and in which:
  said step of selecting specific time points is independent of those certain time points.

10. The method according to claim 9 and:
  utilizing, in said step of selecting specific time points, a relative few time points, as compared to the plurality of certain times employed during the sorption analysis.

11. The method according to claim 2, further including the step of:
  using the temperature changing of a portion of the sample cell as time-dependent data during the sample sorption analysis.

12. The method according to claim 11 including the step of:
  storing, in a look up table, the time-dependent temperature changing data.

13. The method according to claim 1, further including the steps of:
  a) creating experimental data regarding the time-dependent temperature changing of a portion of the sample cell;
  b) forming a time-dependent experimental curve from that experimental temperature data;
  c) matching a curve-fitting formula to that time-dependent experimental curve; and
  d) employing that curve fitting formula in said correcting step f) for correcting for such time-dependent errors.

14. The method according to claim 13 which, said step of matching includes:
  a) selecting specific time points from the experimental temperature curve; and
  b) inserting those time points into the curve fitting formula to enhance said matching.

15. The method according to claim 14 in which, the sorption analysis ascertains data at certain times, and in which:
  said step of selecting specific time points is independent of those certain time points.

16. The method according to claim 15 and:
  utilizing, in said step of selecting specific time pints, a relative few time points, as compared to the plurality of certain times employed during the sorption analysis.

17. The method according to claim 1, in which one of the time-dependent errors is the volume of adsorptive gas adsorbed by the sample in the sample cell, and:
  employing, in said method step of correcting, the equation:

$$(V_{ADS}) = (\Sigma V_{TRANS}) - (V_{TC} + V_{WARM\ ZONE} + V_{COLD\ ZONE}),$$

in which ($V_{ADS}$) is the corrected volume of the adsorptive gas; ($\Sigma V_{TRANS}$) is the actual volume of the adsorbed gas; and ($V_{TC}$) is an amount value obtained as the result of said step of compensating.

18. The method according to claim 17, and:
  obtaining, by said step of compensating, the amount value ($V_{TC}$) by the equation:

$$V_{TC} = \pi (r\ cell^2) \cdot (\Delta H) + (T/77.4) \cdot P/760,$$

in which; ($r\ cell^2$) is the radius of the stem portion of the sample cell cited in said step d) of claim 1; ($\Delta H$) is the changing of the coolant level; and (T) is the time-dependent temperature changing at the stem portion of the sample cell.

19. The method according to claim 18, further including the step of:

establishing at least one of ($\Delta H$) and (T) by experimentation.

20. The method according to claim 19, and: accomplishing said step of establishing off-line, over a length of time, and thereby attaining time-dependent values for at least one of ($\Delta H$) and (T).

21. The method according to claim 20, further including the steps of:

matching a curve fitting formula to those time-dependent values; and substituting resulting curve fit values for at least one of ($\Delta H$) and (T) into the equation ($V_{TC}$).

* * * * *